US010159520B2

(12) United States Patent
Krickeberg et al.

(10) Patent No.: US 10,159,520 B2
(45) Date of Patent: Dec. 25, 2018

(54) DEVICE FOR FIXING A FEMUR FOR HIP ENDOPROSTHESIS SURGERY

(71) Applicant: MAQUET GMBH, Rastatt (DE)

(72) Inventors: Thomas Krickeberg, Karlsbad (DE); Marcel Brauer, Baden-Baden (DE); Holger Dorr, Rastatt (DE)

(73) Assignee: MQUET GMBH, Rastatt (DE)

( * ) Notice: Subject to any disclaimer, the term of this patent is extended or adjusted under 35 U.S.C. 154(b) by 874 days.

(21) Appl. No.: 14/403,301

(22) PCT Filed: Jun. 14, 2013

(86) PCT No.: PCT/EP2013/062397
§ 371 (c)(1),
(2) Date: Nov. 24, 2014

(87) PCT Pub. No.: WO2013/189854
PCT Pub. Date: Dec. 27, 2013

(65) Prior Publication Data
US 2015/0094780 A1    Apr. 2, 2015

(30) Foreign Application Priority Data

Jun. 18, 2012  (DE) .................. 10 2012 105 264

(51) Int. Cl.
*A61B 17/88*  (2006.01)
*A61G 13/10*  (2006.01)
(Continued)

(52) U.S. Cl.
CPC .......... *A61B 17/88* (2013.01); *A61B 17/8866* (2013.01); *A61G 13/0081* (2016.11);
(Continued)

(58) Field of Classification Search
CPC ............ A61G 13/0081; A61G 13/1245; A61B 17/8866; A61B 2017/0275; A61B 2090/571
See application file for complete search history.

(56) References Cited

U.S. PATENT DOCUMENTS 2,459,729 A * 1/1949 Treace ................ A61B 6/0421
378/180
4,558,697 A * 12/1985 Wu ........................ A61B 6/505
606/86 R
(Continued)

FOREIGN PATENT DOCUMENTS

DE       4138317 A1    5/1993
JP    2005-342229 A    12/2005
(Continued)

OTHER PUBLICATIONS

International Search Report for PCT/EP2013/062397 dated Sep. 6, 2013.
(Continued)

*Primary Examiner* — David Bates
(74) *Attorney, Agent, or Firm* — Aaron M. Miller

(57) ABSTRACT

A device for fixing a femur for hip endoprosthesis surgery is disclosed. The device has a femur support including a hook configured to support the femur in a region of the femur between a greater trochanter and a lesser trochanter, and a shaft connected to the hook. A lever arm includes a column and a cantilever, wherein the femur support is disposed on the cantilever. An adjustment device is attached to an operating table. A holder is configured to couple the column of the lever arm to the adjustment device. The adjustment device has a drive motor for rotating the holder about an axis of rotation perpendicular to an adjustment plane to move the column in the adjustment plane. The adjustment plane is (Continued)

perpendicular to a support surface of the operating table and parallel to a longitudinal axis of the operating table.

29 Claims, 7 Drawing Sheets

(51) Int. Cl.
    *A61G 13/12*      (2006.01)
    *A61G 13/00*      (2006.01)
    *A61B 17/00*      (2006.01)

(52) U.S. Cl.
    CPC ....... *A61G 13/101* (2013.01); *A61G 13/1245* (2013.01); *A61G 13/1295* (2013.01); *A61B 2017/00991* (2013.01)

(56) References Cited

U.S. PATENT DOCUMENTS

| | | | | |
|---|---|---|---|---|
| 4,624,245 | A * | 11/1986 | Mullin | A61G 13/12 5/621 |
| 4,979,949 | A * | 12/1990 | Matsen, III | A61B 17/15 414/9 |
| 5,372,597 | A * | 12/1994 | Hotchkiss | A61B 17/6425 602/20 |
| 5,608,934 | A * | 3/1997 | Torrie | A61G 13/0036 5/624 |
| 5,645,079 | A * | 7/1997 | Zahiri | A61F 5/3769 128/882 |
| 5,806,117 | A * | 9/1998 | Gotfried | A61G 13/12 5/601 |
| 6,003,176 | A * | 12/1999 | Wasley | A61G 13/12 128/845 |
| 6,298,507 | B1 * | 10/2001 | Clyburn | A61G 13/12 248/445 |
| 6,311,349 | B1 * | 11/2001 | Kazakia | A61G 13/12 128/845 |
| 6,315,718 | B1 * | 11/2001 | Sharratt | A61B 17/02 600/228 |
| 7,669,602 | B2 * | 3/2010 | McGinnis | A61B 6/0421 128/845 |
| 7,824,353 | B2 * | 11/2010 | Matta | A61B 17/8866 600/201 |
| 8,518,051 | B2 * | 8/2013 | Shoham | A61B 17/157 128/882 |
| 9,333,137 | B1 * | 5/2016 | Hernandez | A61G 7/07 |
| 2002/0157186 | A1 * | 10/2002 | VanSteenburg | A61G 13/04 5/621 |
| 2003/0178027 | A1 * | 9/2003 | DeMayo | A61G 13/12 128/845 |
| 2007/0251011 | A1 * | 11/2007 | Matta | A61B 19/0248 5/624 |
| 2008/0045967 | A1 * | 2/2008 | Lubinus | A61B 17/8866 606/90 |
| 2008/0228191 | A1 * | 9/2008 | Downs | A61B 17/025 606/90 |
| 2008/0289636 | A1 * | 11/2008 | Lacroix | A61G 13/12 128/845 |
| 2013/0191995 | A1 * | 8/2013 | Bellows | A61G 13/0036 5/624 |
| 2015/0073420 | A1 * | 3/2015 | Bookwalter | A61B 17/025 606/90 |
| 2017/0231612 | A1 * | 8/2017 | Termanini | A61B 17/025 606/90 |

FOREIGN PATENT DOCUMENTS

| | | |
|---|---|---|
| JP | 2008-511406 A | 4/2008 |
| JP | 2009-504262 A | 2/2009 |
| KR | 10-2007-0088545 A | 8/2007 |
| KR | 10-2008-0059377 A | 6/2008 |
| WO | 2006/028788 A2 | 3/2006 |
| WO | 2007/021806 A2 | 2/2007 |
| WO | WO2016/196619 A1 * | 12/2016 |

OTHER PUBLICATIONS

Japanese Office Action dated Dec. 15, 2015 issued for corresponding Japanese Patent Application No. 2015-516634, 3 pages.
Korean Office Action dated Feb. 19, 2016 issued for corresponding Korean Patent Application No. 10-2015-7000982, 9 pages.

* cited by examiner

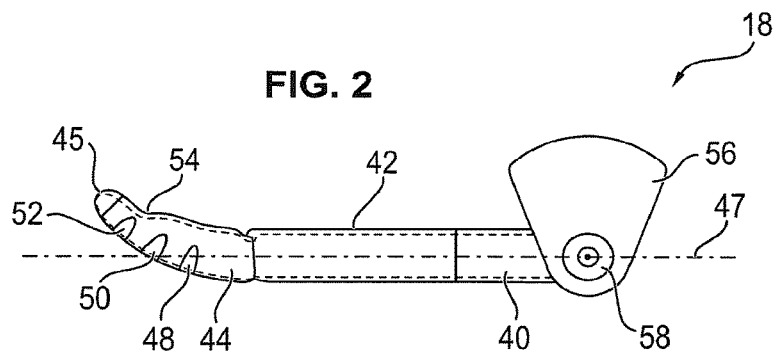
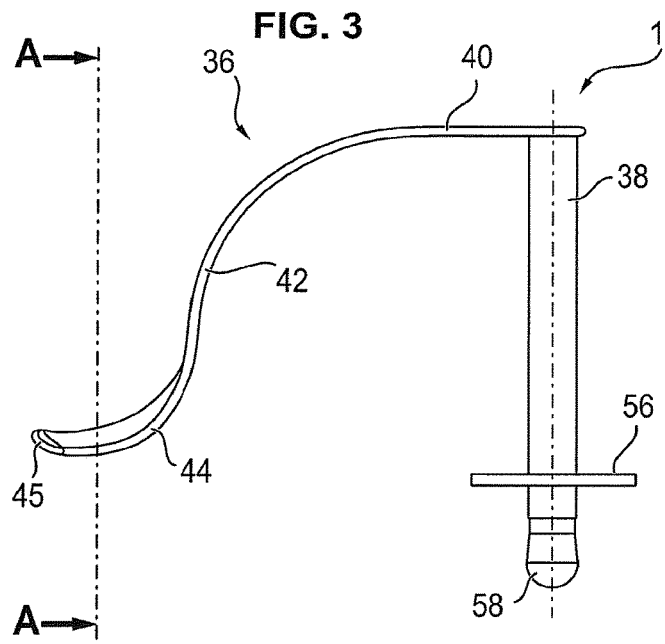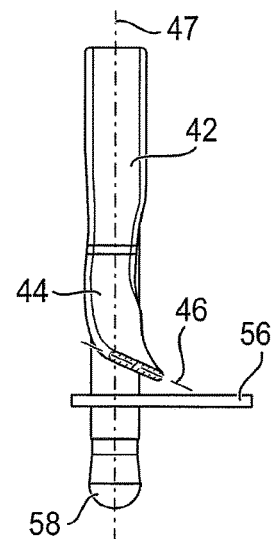
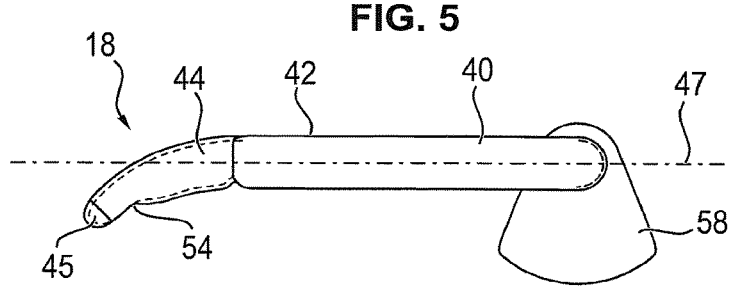

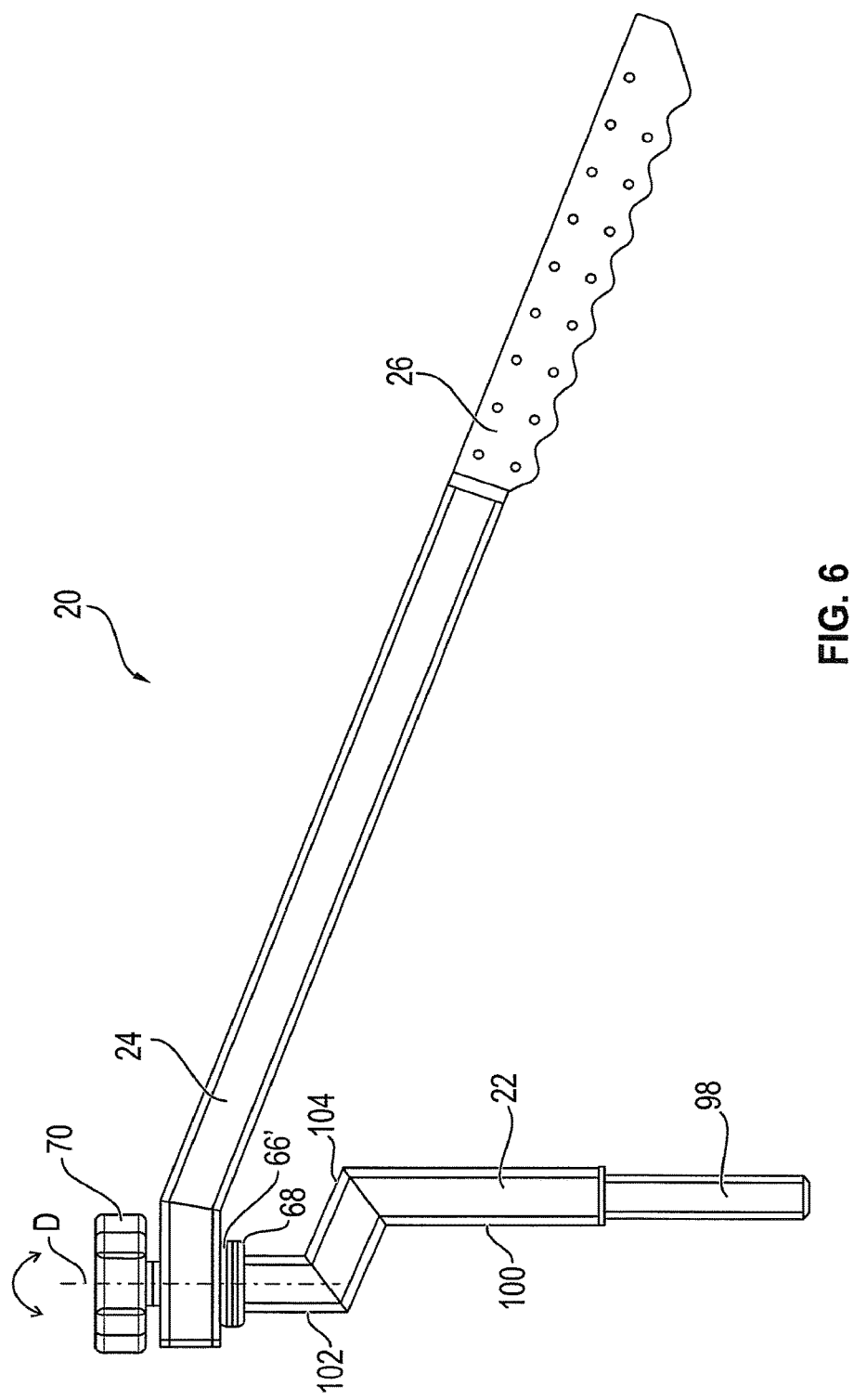

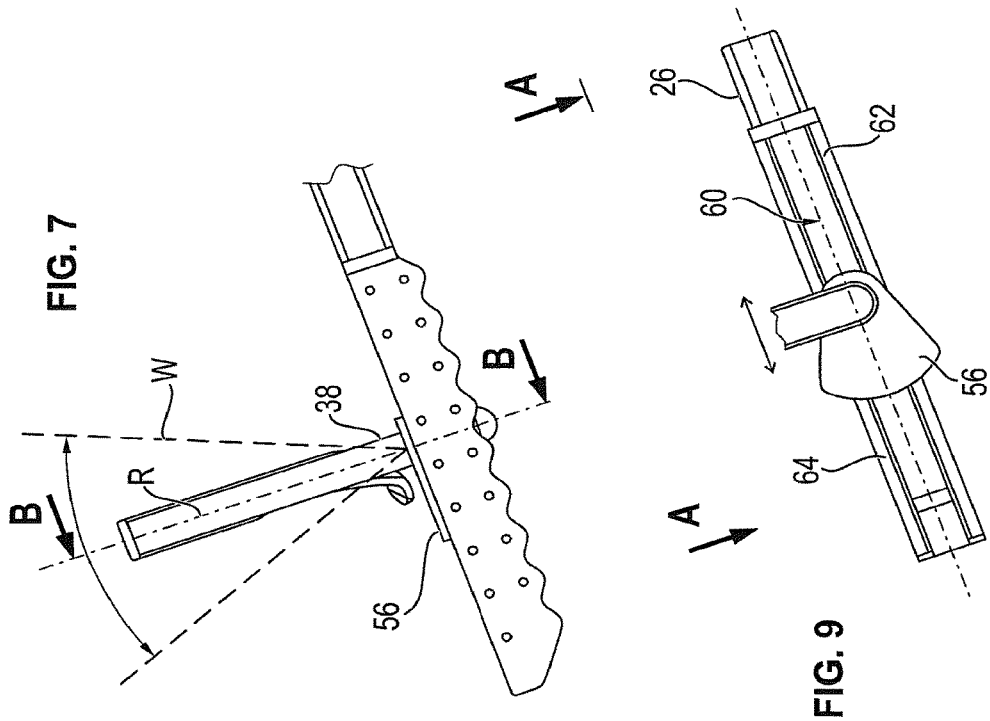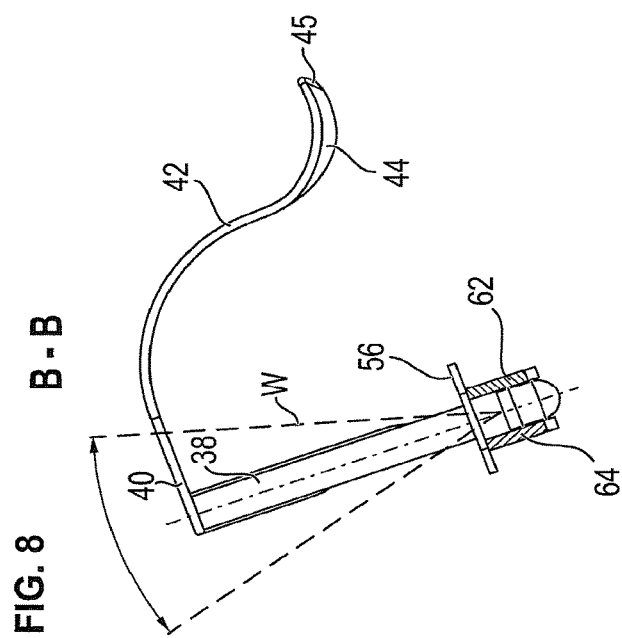

DEVICE FOR FIXING A FEMUR FOR HIP ENDOPROSTHESIS SURGERY

CROSS REFERENCE TO RELATED APPLICATIONS

This application is entitled to the benefit of and incorporates by reference subject matter disclosed in International Patent Application No. PCT/EP2013/062397 filed on Jun. 14, 2013 and German Patent Application No. 10 2012 105 264.6 filed Jun. 18, 2012.

TECHNICAL FIELD

The invention relates to a device for fixing a femur in hip endoprosthetics.

BACKGROUND

During an operation for minimally invasive hip endoprosthetics with anterior approach the femur head is cut off and removed. After cutting off of the femur head the remaining femur has to be stabilized and fixed in order to prevent lowering of the thigh due to the dead weight of the leg. Further, it has to be ensured that the surgeon performing the operation permanently has an optimal access to the femur. For this, the femur has to be slightly raised.

The above-mentioned measures are realized in the prior art in the following manner. First, a support of the femur without auxiliary means provided specifically for this purpose is considered. In this case, the surgeon or his assistant raises the femur manually, if required.

As technical auxiliary means often a cushioned roll is used, which is arranged below the thigh to support the femur indirectly. Also an indirect support by means of a suitable support arranged below the buttocks is possible.

From the prior art further devices are known which allow for a direct support at the bone by means of a femur support specifically provided for this purpose. Such a device is for example described in U.S. Pat. No. 7,824,353 B2. This prior art device comprises a femur support having a bent hook part and a shaft connected to the hook part. The shaft is attached to a longitudinal cantilever, which, in turn, is mounted on a vertical column pivotably about the longitudinal axis thereof. The column is coupled with an adjustment device which allows for moving the column and thus the cantilever and the femur support received at the cantilever in the vertical direction. This movement takes place in an adjustment plane, which is placed perpendicularly to the lying surface of the operating table and in parallel to the longitudinal direction thereof. For realization of this movement the adjustment device has a rotation shaft placed in the adjustment plane, which is for example operated by means of a crank in order to move the femur support linearly in the vertical direction in this manner.

The solution to move the femur support in the adjustment plane as disclosed in U.S. Pat. No. 7,824,353 B2 is comparatively complex. Thus, it takes in particular trouble to operate the rotation shaft placed in the adjustment plane for example by means of a crank in order to move the femur support in the adjustment plane. Also the linear movement of the femur support in the adjustment plane is not always suited to stabilize the femur in the desired manner.

SUMMARY

It is the object of the invention to develop a device determined for fixing a femur of the above explained type further such that it can in particular with respect to the adjustment of the femur support be handled in an easy manner.

The invention solves this object by comprising a femur support having a bent hook part that forms a supporting rest for the femur to be fixed in the region between greater trochanter and lesser trochanter, and having a shaft connected to the hook part, a lever arm having a column and a cantilever, which has a receptacle for attaching the shaft, an adjustment device attached to an operating table, and a holder coupleable to the adjustment device, at which holder the column of the lever arm is attachable, wherein the adjustment device has a drive for moving the column in an adjustment plane, which is placed perpendicularly to the lying surface of the operating table and in parallel to the longitudinal direction thereof, wherein the adjustment device has an axis of rotation placed perpendicularly to the adjustment plane, about which axis of rotation the holder is rotatable in the adjustment plane by means of the drive in order to pivot the column. Advantageous embodiments are indicated in the sub-claims.

The device according to the invention has the advantage that the adjustment device has a rotation axis placed perpendicularly to the adjustment plane, about which rotation axis the holder at which the column of the lever arm is attached is rotatable by means of the drive in order to pivot the column in the adjustment plane. In this context, adjustment plane refers to a vertical plane, which is placed perpendicularly with respect to the lying surface of the operating table and in parallel to the longitudinal direction thereof. Correspondingly, the above-mentioned axis of rotation extends horizontally and transversely with respect to the lying surface of the operating table.

As the invention provides for a pivoting movement of the femur support, the latter can be raised and lowered particularly easily, for example by using the leg plate function, provided with an operating table in any case, for pivoting the femur support. Thus, an operating table often disposes of an adjustment device which is designed for pivoting a leg plate in the vertical direction. Such an adjustment device for example has an interface and/or a profile rail suited for receiving a leg plate as well as a drive motor, which pivots the profile rail about a rotation axis. As in minimally invasive hip endoprosthesis surgery, no leg plates are used, such a motor-driven adjustment device according to the invention can now be used for mounting the femur support, e.g, on the profile rail and thus make the pivoting movement thereof in the adjustment plane possible. This facilitates the handling of the device significantly for the surgeon. Also a significant economic benefit is given, as the motor-driven adjustment device, provided in any case, can be used in order to move the femur support in the desired manner.

Preferably, the hook part of the femur support has a straight portion extending perpendicularly from the shaft and a substantially S-shaped portion, adjacent to the straight portion, having an end portion, which forms the support for the femur to be fixed. The tip of this end portion is preferably rounded in order to prevent damage of the surrounding tissue.

In a preferred embodiment, the end portion of the S-shaped portion has at least one notch at its bottom surface, in which an operating instrument is supportable. Preferably, a plurality of such notches is provided, in which for example so-called Hohmann retractors or comparable wound stretchers can be supported. Due to the support of these instruments at the end portion the danger of soft tissue injuries and damage to the bone is minimized.

Preferably, the shaft, the straight portion of the hook part and a part of the S-shaped portion adjacent to the straight portion are placed on a plane, while the end portion of the S-shaped portion is curved into a direction facing away from this plane. This shape of the femur support allows for a particularly stable contact at the bone between greater trochanter and lesser trochanter. It goes without saying that for the treatment of the right and the left femur two variants of the femur support with mirror-inverted shaping are required.

Advantageously, the curved end portion of the S-shaped portion has a recess on the side thereof facing in said direction. Thus, this recess is positioned at the inner radius of the end portion and has the purpose to prevent contact with soft tissues in the region of the support surface of the end portion.

Preferably, the hook part of the femur support is formed from a profile, which has a flat profile cross section. This flat profile cross section results in the hook part being formed resilient, whereby increased tension on the bone is absorbed.

In a particularly preferred embodiment, the flat profile cross section in the region of the end portion is twisted with respect to the flat profile cross section in the region of the remaining hook part about an angle between 10° and 30°. This means that the end portion is twisted about the previously mentioned angle with respect to the horizontal. This twisted or beveled shaping allows for angular deviations of the femur due to the lowering of the leg. It further allows adjusting the femur preferably by using the leg plate function of the operating table in adduction and abduction. Further, this shaping provides for the femur always having an optimal support surface at the end portion of the femur support.

While the hook part is formed resilient the shaft of the femur support is preferably bending-resistant. Both the hook part and the shaft of the femur support are for example made of stainless steel.

Preferably, the holder has at least one bushing for receiving the column of the lever arm in a form-closed manner. Thus, the column can be easily inserted into the bushing to fix the lever arm to the holder. If a plurality of bushings is provided, the lever arm can selectively be inserted into one of these bushings in order to position it in the desired manner.

In a particularly preferred embodiment, the bushing and the column have corresponding polygonal cross sections, which respectively have such a symmetry that the column is receivable in at least two different orientations in the bushing. In this embodiment, the column further has two straight column portions parallel offset to each other, which are connected with each other via an angular transition piece. Thus, it is for example possible to bring said column portion at which the cantilever of the lever arm is attached closer to the patient lying on the operating table or to remove it further from the patient. If, for example, the bushing and the column have rectangular cross sections, the column can be inserted into the bushing in at least two different orientations, which are rotated about the column longitudinal axis in an angle of 180°. Depending on the respective selected orientation the parallel offset column portion, on which the cantilever is mounted, then has a greater or smaller distance from the patient.

Preferably, the cantilever is pivotably coupled to the column about the longitudinal axis thereof. This pivotable coupling of the cantilever can for example be achieved in that the cantilever has a first contact surface and the column has a second contact surface facing the first contact surface and that the two contact surfaces are brought in contact with each other by means of a corresponding operating element, e.g. a handle screw, in order to block the pivotability of the cantilever. As contact surfaces for example tooth surfaces can be used, which are pressed onto one another by tightening the handle screw.

In a preferred embodiment, the shaft has a hemispherical end portion, e.g. in the shape of a correspondingly shaped pin. The receptacle of the cantilever is formed from a longitudinal groove in this embodiment, in which the hemispherical end portion of the shaft is insertable in a form-closed manner. The hemispherical design of the shaft end portion allows for it to be inserted into the groove with a certain angular deviation in order to fix the shaft of the femur support to the cantilever. An advantage of this embodiment is that the end portion of the shaft does not have a profile such as e.g. a square, which has to be oriented in an accurately fitting manner with respect to its counter piece (here the groove) so that it can be inserted into the counter piece at all. The shaft of the femur hook can thus be fixed to the cantilever very easily tolerating certain angular deviations at the cantilever. It facilitates the handling during the surgery significantly.

In a specific embodiment, the cantilever is preferably formed from at least two parts, one of these parts being movable like a telescope against the other part for the length adjustment of the cantilever. The length adjustment of the cantilever makes it even easier to position the femur support as desired.

In order to lock the length adjustment, preferably one of the two parts of the cantilever has a latch element and the other part a plurality of latch openings for receiving the latch element.

BRIEF DESCRIPTION OF THE DRAWINGS

The invention will be explained in more detail in the following on the basis of the Figures, wherein:

FIG. 2 shows a bottom view of a femur support;

FIG. 3 shows a side view of the femur support;

FIG. 4 shows a sectional front view of the femur support;

FIG. 5 shows a top view of the femur support;

FIG. 6 shows a side view of a lever arm formed from a column and a cantilever;

FIG. 7 shows a side view showing the femur support attached to the cantilever;

FIG. 8 shows a further, partially sectional view showing the femur support attached in the receptacle of the cantilever;

FIG. 9 shows a top view showing a part of the femur support attached in the receptacle of the cantilever;

DETAILED DESCRIPTION

Figure 1:
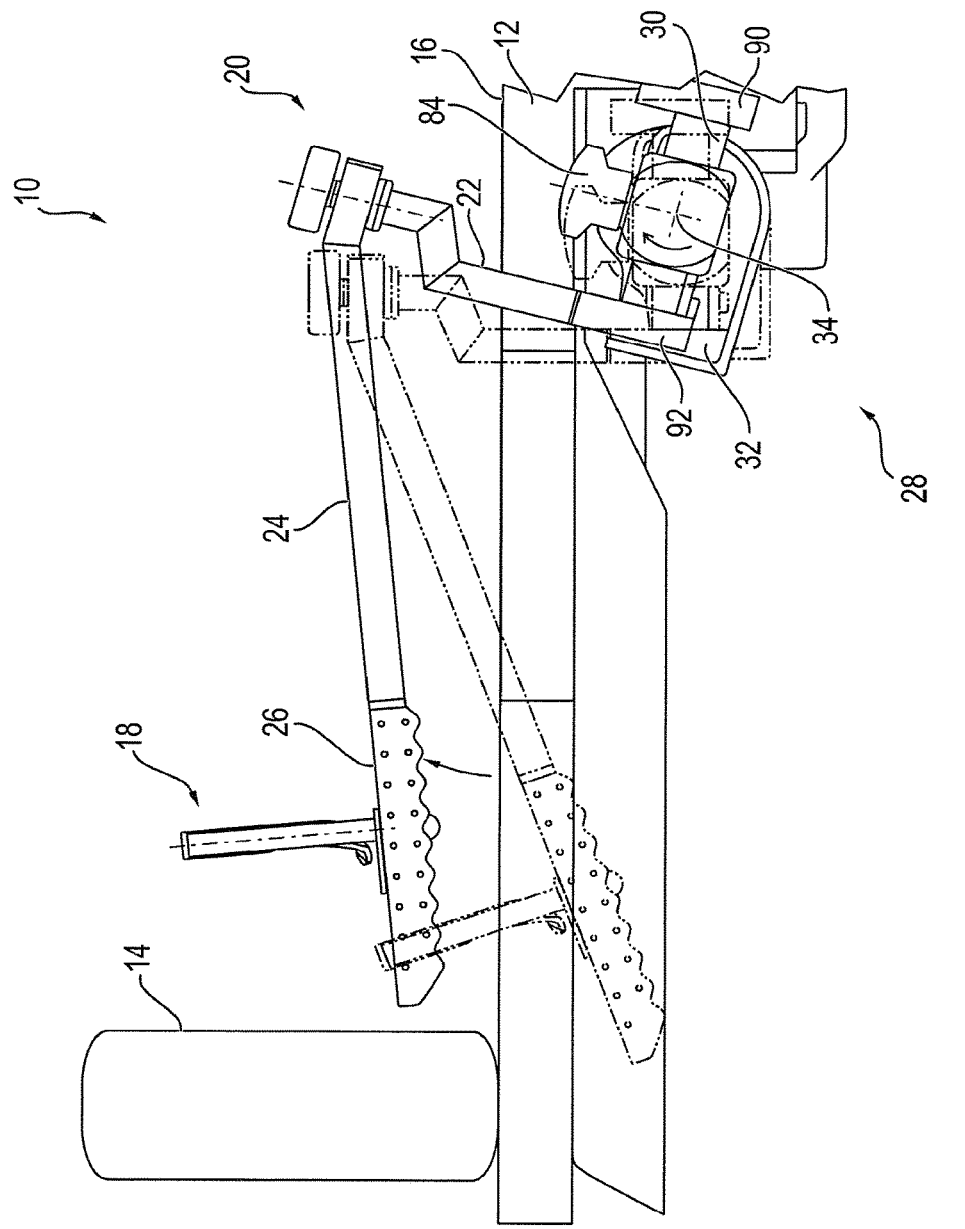
FIG. 1 shows a side view of a device attached to an operating table, which constitutes an embodiment of the invention.

FIG. 1 is a side view showing a device 10 according to the invention as embodiment. The device 10 serves to support a femur, not being shown, during an operation for minimally invasive hip endoprosthetics. It is mounted on an operating table 12 on which the patient to be operated is to be supported. In FIG. 1, further a support roll 14 is shown, which is attached on a support surface 16 of the operating table 12.

The device 10 comprises a femur support 18 described later in detail, a lever arm 20, which is formed from a column 22 and a cantilever 24. The cantilever 24 has a receptacle 26, in which the femur support 18 is attached.

The device 10 further comprises an adjustment device 28 mounted on a side surface of the operating table 12, which adjustment device 28 serves to pivot the lever arm 20 in a vertical adjustment plane. In FIG. 1, two pivoting positions of the lever arm 20 are shown, one of which is indicated by dashed lines. The adjustment plane, in which the lever arm 20, as indicated by the arrow in FIG. 1, is pivoted by means of the adjustment device 28, is placed perpendicularly to the lying surface 16 of the operating table 12 and in parallel to the longitudinal direction thereof. The adjustment plane is thus placed in parallel to the drawing plane of FIG. 1.

The device 10 has a holder 30 coupleable with the adjustment device 28, to which holder 30 the lever arm 20 is attached. The adjustment device 28 has a drive motor 32, which serves to rotate the holder 30 about a horizontal rotation axis 34, which is placed perpendicularly to the previously mentioned adjustment plane. In the present embodiment, the drive motor 32 can also be used in another application in order to pivot a leg plate, not being shown, in the adjustment plane.

In the following, the femur support 18 is described in detail, referring in particular to FIGS. 2 to 5.

As can best be seen in FIG. 3, the femur support 18 is formed from a hook part 36 and a shaft 38. The hook part 36 has over its entire length a flat profile cross section and is thus formed resilient. In contrast, the shaft 38 has a circular cross section. It is thus formed bending-resistant.

The hook part 36 has a straight portion 40 extending perpendicularly from the shaft 38, which straight portion 40 turns into a substantially S-shaped curved portion 42. At the free end of the S-shaped portion 42 a rounded end portion 44 is positioned, which is determined to contact the femur between greater trochanter and lesser trochanter. The end portion 44 has a rounded tip 45 without sharp edges. Thus, it can be inserted into the wound without damaging the tissue coming into contact therewith.

As the bottom view according to FIG. 2, the sectional front view according to FIG. 4 and the top view according to FIG. 5 show the femur support 18 is shaped substantially such that it is substantially placed in one plane with the exception of the end portion 44. In FIGS. 2, 4 and 5, this plane is arranged perpendicularly to the drawing plane and indicated therein with the reference sign 47. In contrast, the end portion 44 is curved into a direction facing away from the plane 47. This is in particular visible in FIGS. 2 and 5.

Further, the flat profile cross section of the hook part 36 in the region of the end portion 44 is twisted by a predetermined angle with respect to the flat profile cross section in the region of the remaining hook part. This twist is indicated in FIG. 4 by the cross section indicated with the line 46, which is inclined at the predetermined angle with respect to the horizontal. In the present embodiment, the inclination angle measures approximately 25°. The upper surface of the end portion 44 thus forms a beveled support surface which allows lowering the extended leg of the patient in a variable angle (e.g. between −10° and −30° with respect to the horizontal and at the same time constituting an optimally supporting support for the femur.

The largely vertical portion of the hook part 36, which is positioned between the end portion 44 and the straight portion 40, i.a. has the function of protecting the soft tissues of the patient against the instrument contact. The flat profile cross section of the hook part 36 contributes to this purpose.

As shown in FIG. 2, the end portion 44 of the hook part 36 has a plurality of notches 48, 50 and 52 at its bottom surface. In these notches 48, 50, 52 surgery devices such as Hohmann retractors or wound stretchers can be supported. By means of this support, soft tissue injuries and bone damages are prevented.

As in particular FIGS. 2 and 5 show, the curved end portion 44 of the hook part 36 at the side pointing in the direction of curvature (in FIG. 2 top left and in FIG. 5 bottom left) has a recess 54 having the purpose of preventing the contact with soft tissues in the region of the support surface.

As can best be seen in FIGS. 3 and 4, the shaft 38 has a support plate 56 in the region of its free end, which serves for supporting oneself on the receptacle 26 of the lever arm 20 (cf. FIG. 7). Further, the free end of the shaft 38 is formed as hemispherical end portion 58, i.e. as an end portion, which extends in a convex or tapered manner. The function of this end portion 58 formed in the shape of a hemispherical pin is illustrated in FIGS. 7 and 8.

FIGS. 7 and 8 show the femur support 18 in a state, in which it is inserted into the receptacle 26 of the lever arm 20. The lever arm 20 provided with the receptacle 26 is shown again individually in FIG. 6. As shown therein, the receptacle 26 is positioned at the free end of the cantilever 24 of the lever arm 20.

As shown in FIG. 9, the receptacle 26 is formed from a longitudinal groove 60, which has two opposing contact surfaces 62 and 64 (cf. also FIG. 8). The hemispherical design of the end portion 58 allows the operator to insert the shaft 38, which serves at the same time as handle, with a tolerable angular deviation with respect to a predetermined inserting direction into the groove 60. This situation is in particular illustrated in FIGS. 7 and 8, in which the above-mentioned predetermined inserting direction is referred to with R and the angular deviation tolerable with respect thereto is referred to with W. In contrast to e.g. a square the hemispherical end portion 58 does not constitute a profile, which has to be oriented in an accurately fitting manner with respect to the groove 60, so that it can be inserted into the groove 60 at all. Rather, the hemispherical design of the end portion 58 allows for it to support itself at various supporting points on the contact surfaces 62 and 64 of the groove 60, while it is inserted into the groove 60. In this manner, the angular range W illustrated in FIGS. 7 and 8 is realized, within which the shaft 38 can be oriented, when it is inserted into the groove 60, without tilting so much that an insertion of the end portion 58 into the groove 60 becomes impossible.

If the end portion 58 is received completely in the groove 60 it contacts the contact surfaces 62 and 64. Further, in this state the support plate 56 lies on the upper surface of the groove 60. By means of the supporting force the end portion 58 is in the inserted state securely fixed in the groove 60. As illustrated in FIG. 9 by the double arrow, in this manner the shaft 38 of the femur support 18 can be easily and securely inserted at any point along the groove 60.

As shown in FIG. 6, the cantilever 24 is pivotably mounted about a vertical axis of rotation D at the column 22. The parts of the cantilever 24 and the column 22 coupled with each other are thereby respectively provided with a tooth surface 66 or 68, which can be pressed onto each other via a handle screw 70 in order to block the rotation of the cantilever 24 about the vertical pivot axis D. Thus, the cantilever 24 can be locked in a desired pivot position.

The embodiment illustrated in FIG. 6 provides the possibility to pivot the cantilever 24 away from the patient, if required, in order to have a better access to the femur.

Figure 11:
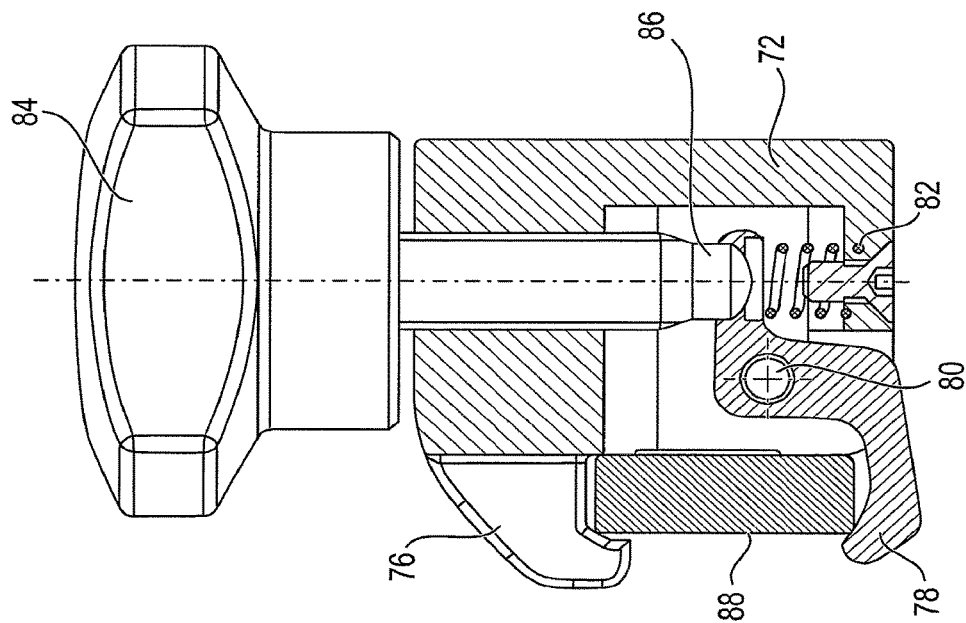
FIG. 11 shows a sectional view of the holder.
Figure 10:
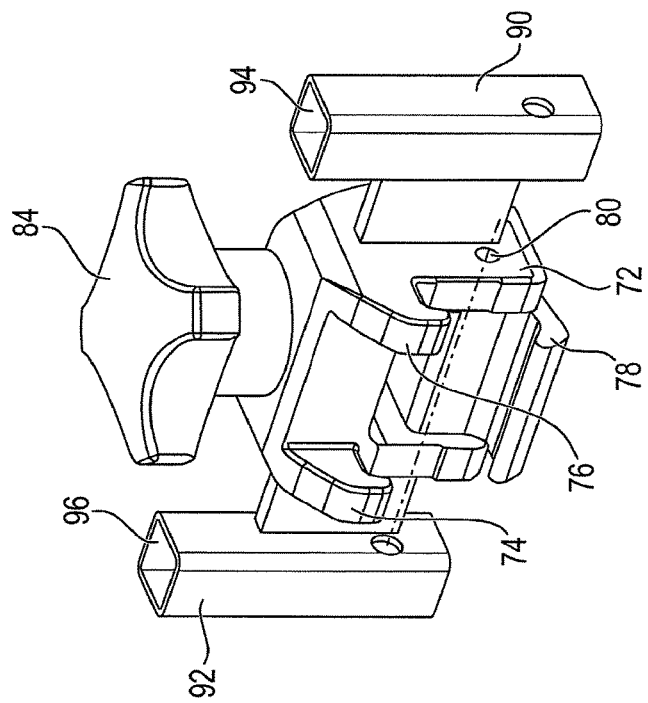
FIG. 10 shows a perspective view of a holder to which the lever arm is attachable.

In FIGS. 10 and 11, the holder 30 provided in the device 10 is illustrated in more detail.

The holder 30 has a housing 72, which has a substantially L-shaped cross section. At the housing 72 two jaw-shaped projections 74 and 76 are positioned, which cooperate with a clamping piece 78. The clamping piece 78 is supported on a bearing bolt 80 and biased via a pressure spring 82, which supports itself against the housing 72 and a leg of the clamping piece 78, into an open position. In this open position, the jaw-shaped projections 74 and 76 on the one hand and the clamping piece 78 on the other hand have the largest possible vertical distance with respect to each other.

Into the housing 72 a handle screw 84 is screwed from above, the free end 86 of which presses onto the clamping piece 78. If the handle screw 84 is closed, the clamping piece 78 is pivoted clockwise about the bearing bolt 80 in FIG. 11.

The housing 72 is clamped via the two jaw-shaped projections 74, 76 and the clamping piece 78 at a profile rail 88, which is mounted on the adjustment device 28. For this, the housing 72 in a state, in which the projections 74, 76 and the clamping piece 78 have the largest possible vertical distance with respect to each other, are stuck on the profile rail 88 such, that said profile rail 88 is received in the space between the projections 74, 76 and the clamping piece 78. Then the handle screw 84 is closed in order to pivot the clamping piece 78 against the biasing force exerted by the pressure spring 82 in order to pivot the bearing bolt 80. Thus, the profile rail 88 is clamped between the projections 74, 76 and the clamping piece 78. Thereby the housing 72 contacts the profile rail 82 at four points, i.e. the two projections 74, 76 and the housing end faces positioned below the projections 74, 76.

The housing 72 has two bushings 90 and 92 on its side surfaces facing away from each other. The bushings 90, 92 respectively have a through-hole 94 or 96 having a rectangular cross section. The openings 94 and 96 serve for receiving the free end, referred to with 98 in FIG. 6, of the column 22. This free end 98 of the column 22 is corresponding to the cross section shape of the respective opening 94, 96 formed as square. Thus, it can be inserted in a form-closed manner into each of the openings 94 and 96. For locking in the respective opening 94, 96 the free end 98 of the column 22 e.g. has a securing pin, which is not illustrated in the Figures.

Due to the cross section shape of the openings 94, 96 and the end portion 98 the latter can be inserted in different orientations into the respective opening 94, 96. This can be used for increasing or reducing the distance, which the pivoting axis D, shown in FIG. 6, about which the cantilever 24 is pivotable, has with respect to the patient. For this, the column 22 is formed from two straight column portions 100, 102 parallel offset to each other and an angular transition piece 104, which connects the parallel offset column portions 100, 102 to each other. Depending on the orientation of the end portion 98 inside the respective bushing 94 or 96 in this way the column portion 102 through which the pivoting axis D extends can be brought closer to the patient or removed from him.

Figure 12:
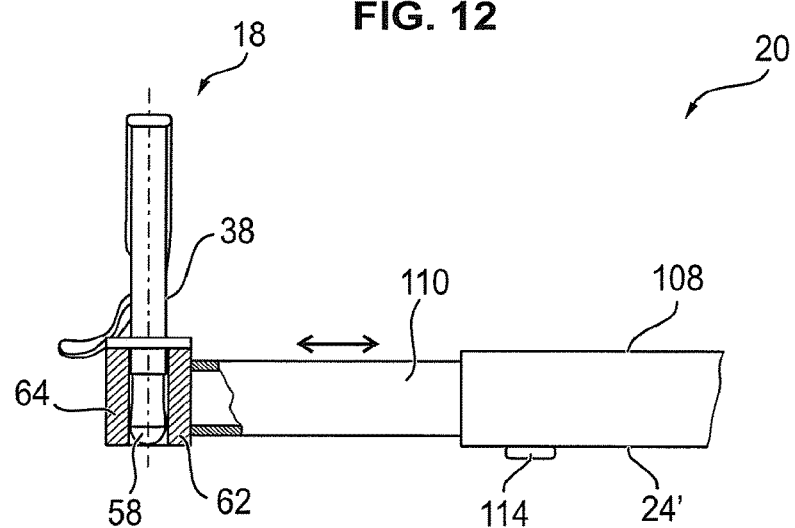
FIG. 12 shows a partially sectional side view of a modified embodiment of the cantilever.
Figure 13:
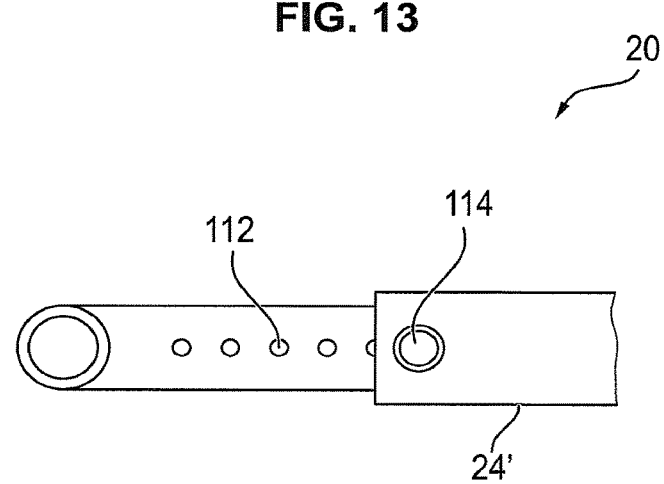
FIG. 13 shows a bottom view of the cantilever according to FIG. 12.
Figure 14:
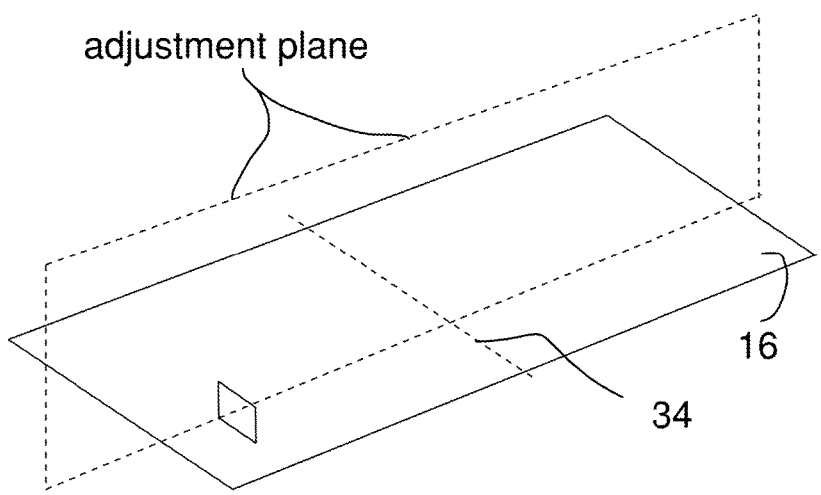
FIG. 14 shows a non-limiting representation of the adjustment plane, the lying surface, and the rotational axis according to certain example embodiments of the present disclosure.

In FIGS. 12 and 13, a modified form of the cantilever of the lever arm 20 is illustrated and is referred to with 24' therein. The cantilever 24' is formed from a first part 108 and a second part 110, which is received slidably like a telescope in the first part 108 as indicated in FIG. 12 by the double arrow. By the second part 110 being pulled out of or pushed into the first part 108 the length of the cantilever 24' can be varied.

The locking of this length adjustment is carried out by a latch element, not shown in FIGS. 12 and 13, formed at the first part 108, latching during the movement of the second part 110 automatically into one of a plurality of latch openings 114, which are formed at the second part 110. Via an operating element 114 cooperating with the latch element the locking can be released again.

The embodiment illustrated in FIGS. 12 and 13 has the advantage that releasing of the locking and the adjustment of the length of the cantilever 24' can be carried out simultaneously with one hand.

Although various embodiments of the present invention have been described and shown, the invention is not restricted thereto, but may also be embodied in other ways within the scope of the subject-matter defined in the following claims.

What is claimed is:

1. A device for fixing a femur, the femur having a greater trochanter and lesser trochanter, the device comprising:
    a femur support having a bent hook part that forms a supporting rest for the femur to be fixed, and a shaft connected to the hook part;
    a lever arm having a column and a cantilever, the cantilever comprising a receptacle for attaching the shaft;
    an adjustment device configured to be attached to an operating table, and
    a holder coupleable to the adjustment device, at which holder the column of the lever arm is attachable;
    wherein the adjustment device has a drive for rotating the column about an axis of rotation in an adjustment plane, wherein the adjustment plane is oriented perpendicularly to a lying surface of the operating table, when present.

2. The device according to claim 1, wherein the hook part of the femur support has a straight portion perpendicularly extending from the shaft and a substantially S-shaped portion adjacent to the straight portion and having an end portion which forms the rest for the femur to be fixed.

3. The device according to claim 2, wherein the end portion of the S-shaped portion is rounded.

4. The device according to claim 2, wherein the end portion of the S-shaped portion has at least one notch at its bottom surface, in which a surgery device is supportable.

5. The device according to claim 2, wherein the shaft, the straight portion of the hook part and a part of the S-shaped portion adjacent to the straight portion are disposed in a second plane, and the end portion of the S-shaped portion is curved in a direction pointing away from the second plane.

6. The device according to claim 5, wherein the curved end portion of the S-shaped portion has a recess on its side pointing into said direction.

7. The device according to claim 1, wherein the hook part of the femur support comprises at least one elongated flat surface.

8. The device according to claim 7, wherein the at least one elongated flat surface in the region of the end portion is twisted by an angle set between 10° and 30° with respect to the at least one elongated flat surface in the region of the remaining hook part.

9. The device according to claim 1, wherein the shaft of the femur support is formed to be resistant to bending.

10. The device according to claim 1, wherein the holder has at least one bushing for receiving the column of the lever arm.

11. The device according to claim 10, wherein the bushing and the column have polygonal cross-sections corresponding to each other, which have respectively such a symmetry that the column is receivable in at least two different orientations in the bushing, and
the column has two straight column portions parallel and offset with respect to each other, which are connected to each other via a transition piece.

12. The device according to claim 1, wherein the holder has a profile rail attachable to an operating table, and the holder has at least one jaw-shaped projection, a clamping piece biased via a spring element into an open position and an operating element, with which the clamping piece, while decreasing its distance from the projection, is movable against a biasing force exerted by the spring element into a closed position, wherein the profile rail in the open position is receivable in a space between projection and clamping piece and in the closed position is clamped between the projection and the clamping piece.

13. The device according to claim 12, wherein
the clamping piece is pivotably supported on a bearing bolt between its open position and its closed position, and
the operating element is a manually operable handle screw, which for pivoting the clamping piece into the closed position presses against the biasing force exerted by the spring element onto the clamping piece.

14. The device according to claim 1, wherein the cantilever is coupled pivotably to the column about a longitudinal axis thereof.

15. The device according to claim 14, wherein the cantilever has a first contact surface and the column has a second contact surface facing the first contact surface, and the two contact surfaces can be brought in contact with each other in order to block the pivotability of the cantilever.

16. The device according to claim 1, wherein the shaft has a hemispherical end portion, and the receptacle of the cantilever is formed from a longitudinal groove in which the hemispherical end portion of the shaft is insertable.

17. The device according to claim 1, wherein the cantilever is formed from at least two parts, one of said parts being movable like a telescope against the other part for length adjustment of the cantilever.

18. The device according to claim 17, wherein one of the two parts of the cantilever has a latch element and the other part has a plurality of latch openings for receiving the latch element.

19. The device according to claim 3, wherein the end portion of the S-shaped portion has at least one notch at its bottom surface, in which a surgery device is supportable.

20. The device according to claim 3, wherein the shaft, the straight portion of the hook part and a part of the S-shaped portion adjacent to the straight portion are placed on a plane, and
the end portion of the S-shaped portion is curved in a direction pointing away from this plane.

21. The device of claim 1, wherein the adjustment plane is parallel to a longitudinal direction of the lying surface of the operating table, when the device is attached to said operating table.

22. The device of claim 1, wherein the holder is rotatable in the adjustment plane about the axis of rotation of the adjustment device to permit pivoting of the column in the adjustment plane.

23. A device for fixing a femur, the device comprising:
a femur support comprising:
a hook configured to support the femur, and
a shaft connected to the hook;
a lever arm configured to support and position the femur support;
an adjustment device for attachment to an operating table;
the adjustment device configured to pivotably move the lever arm and femur support about a horizontal axis;
the adjustment device also being configured so that said pivotal movement of the lever arm and femur support about the horizontal axis moves at least part of the lever arm within an adjustment plane;
wherein when the device is attached to an operating table:
the adjustment plane is oriented vertically, is perpendicular to a support surface of the operating table, and is perpendicular to the horizontal axis.

24. The device of claim 23, wherein movement of the lever arm within the adjustment plane is caused by a motor.

25. The device of claim 23,
wherein the horizontal axis passes under the support surface of the operating table, when present; and
wherein the adjustment plain is parallel to a longitudinal dimension of the support surface of the operating table, when present.

26. The device of claim 1, wherein the adjustment plane is parallel to a longitudinal direction of the operating table, when present.

27. The device of claim 1,
wherein the adjustment device is attached to an operating table; and
wherein the adjustment device is further configured to pivot a leg plate of the operating table vertically.

28. A device useful for minimally invasive hip surgery, the device usable with an operating table having a lying surface, the device comprising:
a femur support for supporting a patient's femur, the femur support having a curved hook that forms a supporting rest for supporting the patient's femur, and a shaft connected to the curved hook;
a lever arm having a column and an longitudinal extension extending at an angle to the column, the longitudinal extension comprising a receptacle for attaching with the shaft of the femur support;
a pivot adjustment device configured to be attached to the operating table, when present;
a holder configured to be coupled to the pivot adjustment device;
wherein the column of the lever arm is attachable to the holder;
wherein the pivot adjustment device is configured to permit pivotable rotation of the column of the lever arm through the use of a motor about a horizontal axis of rotation in an adjustment plane, wherein the adjustment plane is oriented perpendicularly to the lying surface of the operating table, when present.

29. The device of claim 28, wherein the pivot adjustment device comprises a rail, the rail having a rectangular cross-sectional profile, and the holder is coupled to the pivot adjustment device through use of the rail.

* * * * *